United States Patent
Hu et al.

(10) Patent No.: US 10,401,327 B2
(45) Date of Patent: Sep. 3, 2019

(54) SYSTEMS AND METHODS FOR MULTISPECTRAL PHOTOACOUSTIC MICROSCOPY

(71) Applicant: UNIVERSITY OF VIRGINIA PATENT FOUNDATION, Charlottesville, VA (US)

(72) Inventors: Song Hu, Charlottesville, VA (US); Rui Cao, Charlottesville, VA (US); John A. Hossack, Charlottesville, VA (US); Joseph P. Kilroy, Charlottesville, VA (US)

(73) Assignee: UNIVERSITY OF VIRGINIA PATENT FOUNDATION, Charlottesville, VA (US)

(*) Notice: Subject to any disclaimer, the term of this patent is extended or adjusted under 35 U.S.C. 154(b) by 66 days.

(21) Appl. No.: 15/532,210

(22) PCT Filed: Dec. 8, 2015

(86) PCT No.: PCT/US2015/064543
§ 371 (c)(1),
(2) Date: Jun. 1, 2017

(87) PCT Pub. No.: WO2016/094434
PCT Pub. Date: Jun. 16, 2016

(65) Prior Publication Data
US 2017/0356884 A1 Dec. 14, 2017

Related U.S. Application Data

(60) Provisional application No. 62/088,722, filed on Dec. 8, 2014.

(51) Int. Cl.
*G01N 29/28* (2006.01)
*G02B 21/00* (2006.01)
(Continued)

(52) U.S. Cl.
CPC ......... *G01N 29/2425* (2013.01); *G01N 29/28* (2013.01); *G02B 21/0004* (2013.01);
(Continued)

(58) Field of Classification Search
CPC .. G02B 27/005; G02B 21/0004; G02B 21/02; G02B 27/0025; G01N 29/28; G01N 29/2425; G01N 2291/104
(Continued)

(56) References Cited

U.S. PATENT DOCUMENTS 5,615,675 A * 4/1997 O'Donnell ......... G01N 29/0681
600/425
7,402,136 B2 7/2008 Hossack et al.
(Continued)

FOREIGN PATENT DOCUMENTS

WO  2003075769 A1  9/2003
WO  2004064619 A2  8/2004
(Continued)

OTHER PUBLICATIONS

International Search Report and Written Opinion for Related International Application No. PCT/US2015/064543 dated Feb. 16, 2016, 16 pages.
(Continued)

*Primary Examiner* — Jacques M Saint Surin
(74) *Attorney, Agent, or Firm* — Meunier Carlin & Curfman LLC

(57) ABSTRACT

A reflection-mode multispectral photoacoustic microscopy (PAM) system and related method is disclosed, based on an optical-acoustic objective in communication with an ultrasonic transducer. In some embodiments of the disclosed technology, when aligned and positioned in a predetermined
(Continued)

manner, little to no chromatic aberration is provided, and with convenient confocal alignment of the optical excitation and acoustic detection.

19 Claims, 12 Drawing Sheets

(51) Int. Cl.
G02B 21/02 (2006.01)
G02B 27/00 (2006.01)
G01N 29/24 (2006.01)

(52) U.S. Cl.
CPC .......... *G02B 21/02* (2013.01); *G02B 27/005* (2013.01); *G02B 27/0025* (2013.01); *G01N 2291/104* (2013.01)

(58) Field of Classification Search
USPC ........................................................ 73/643
See application file for complete search history.

(56) References Cited

U.S. PATENT DOCUMENTS

| | | | |
|---|---|---|---|
| 7,699,776 B2 | 4/2010 | Walker et al. | |
| 7,750,537 B2 | 7/2010 | Hossack et al. | |
| 8,057,392 B2 | 11/2011 | Hossack et al. | |
| 8,093,782 B1 | 1/2012 | Hossack | |
| 8,454,512 B2* | 6/2013 | Wang | A61B 5/0059 600/437 |
| 8,622,911 B2 | 1/2014 | Hossack et al. | |
| 9,237,898 B2 | 1/2016 | Hossack et al. | |
| 9,244,160 B2 | 1/2016 | Blalock et al. | |
| 9,275,630 B2 | 3/2016 | Blalock et al. | |
| 9,351,705 B2* | 5/2016 | Wang | A61B 5/0062 |
| 9,442,095 B2* | 9/2016 | Jiao | G01N 29/0681 |
| 9,445,780 B2 | 9/2016 | Hossack et al. | |
| 9,513,260 B2* | 12/2016 | Zhang | G01N 29/0681 |
| 9,526,922 B2 | 12/2016 | Hossack et al. | |
| 9,528,966 B2* | 12/2016 | Wang | A61B 5/0059 |
| 9,833,148 B2* | 12/2017 | Wang | A61B 5/0066 |
| 9,874,545 B2* | 1/2018 | Fukushima | G02B 21/002 |
| 2005/0243876 A1 | 11/2005 | Kung | |
| 2006/0184042 A1 | 8/2006 | Wang et al. | |
| 2006/0262316 A1 | 11/2006 | Baney | |
| 2007/0015992 A1 | 1/2007 | Filkins et al. | |
| 2007/0016022 A1 | 1/2007 | Blalock et al. | |
| 2008/0002199 A1 | 1/2008 | van Beek et al. | |
| 2010/0063399 A1 | 3/2010 | Walker et al. | |
| 2010/0168578 A1 | 7/2010 | Garson, Jr. et al. | |
| 2010/0268042 A1* | 10/2010 | Wang | A61B 5/0059 600/322 |
| 2010/0268086 A1 | 10/2010 | Walker et al. | |
| 2010/0312106 A9 | 12/2010 | Blalock et al. | |
| 2011/0275890 A1 | 11/2011 | Wang et al. | |
| 2012/0029356 A1 | 2/2012 | Hossack et al. | |
| 2012/0204648 A1* | 8/2012 | Wang | A61B 5/0095 73/606 |
| 2012/0330157 A1* | 12/2012 | Mandella | G02B 21/0028 600/443 |
| 2013/0245406 A1 | 9/2013 | Wang et al. | |
| 2014/0046186 A1 | 2/2014 | Mauldin, Jr. et al. | |
| 2015/0011884 A1 | 1/2015 | Walker et al. | |
| 2015/0025387 A1 | 1/2015 | Hossack et al. | |
| 2015/0133788 A1 | 5/2015 | Mauldin, Jr. et al. | |
| 2015/0160120 A1* | 6/2015 | Sun | G01N 21/1702 73/606 |
| 2017/0065182 A1* | 3/2017 | Wang | A61B 5/0095 |

FOREIGN PATENT DOCUMENTS

| | | |
|---|---|---|
| WO | 2004064620 A2 | 8/2004 |
| WO | 2004065978 A2 | 8/2004 |
| WO | 2006042067 A2 | 4/2006 |
| WO | 2008154632 A2 | 12/2008 |
| WO | 2009055720 A1 | 4/2009 |
| WO | 2010021709 A1 | 2/2010 |
| WO | 2011011539 A1 | 1/2011 |
| WO | 2012148985 A1 | 11/2012 |
| WO | 2013163420 A1 | 10/2013 |
| WO | 2013188625 A1 | 12/2013 |
| WO | 2014131631 A1 | 9/2014 |

OTHER PUBLICATIONS

Beard, P., "Biomedical Photoacoustic Imaging," Interface Focus, 2011, 30 pages.

Benjamin, D.I., et al., "Ether Lipid Generating Enzyme AGPS Alters the Balance of Structural and Signaling Lipds to Fuel Cancer Pathogenicity," PNAS, Sep. 2013, vol. 110, No. 37, pp. 14912-14917.

Cai, D.K., et al., "Optical Absorption in Transparent PDMS Materials Applied for Multimode Waveguides Fabrication," Optical Materials, 2008, vol. 30, pp. 1157-1161.

Hanahan, D., et al., "The Hallsmarks of Cancer," Cell, 2000, vol. 100, pp. 57-70.

Hu, S., et al., "Second-Generation Optical-Resolution Photoacoustic Microscopy With Improved Sensitivity and Speed," Optics Letters, Apr. 2011, vol. 36, No. 7, pp. 1134-1136.

Li, L., et al., "Fully Motorized Optical-Resolution Photoacoustic Microscopy," Optics Letters, Apr. 2014, vol. 39, No. 7, pp. 2117-2120.

Li, M-L., et al., "Simultaneous Molecular and Hypoxia Imaging of Brain Tumors in Vivo Using Spectroscopic Photoacoustic Tomography," Proceedings of the IEEE, Mar. 2008, vol. 96, No. 3, pp. 481-489.

Maslov, K., et al., "Optical-Resolution Photoacoustic Microscopy for In Vivo Imaging of Single Capillaries," Optics Letters, May 2008, vol. 33, No. 9, pp. 929-931.

Oh, J-T, et al.,"Three-Dimensional Imaging of Skin Melanoma In Vivo by Dual-Wavelength Photoacoustic Microscopy," Journal of Biomedical Optics, May/Jun. 2006, vol. 11, No. 3, pp. 034032-1 through 034032-4.

Oladipupo, S.S., et al., "Conditional HIF-1 Induction Produces Multistate Neovascularization With Stage-Specific Sensitivity to VEGFR Inhibitors and Myeloid Cell Indepnendence," BLOOD, Apr. 2011, vol. 117, No. 15, pp. 4142-4153.

Oladipupo, S., et al., "VEGF is Essential for Hypoxia-Inducible Factor-Medicated Neovascularization But Dispensable for Endothelial Sprouting," PNAS, Aug. 2011, vol. 108, No. 32, pp. 13264-13269.

Pleitz, M. A., et al., "In Vivo Noninvasive Monitoring of Glucose Concentration in Human Epidermis by Mid-Infrared Pulsed Photoacoustic Spectroscopy," Analytical Chemistry, 2013, vol. 85, pp. 1013-1020.

Santos, C.R., et al., "Lipid Metabolism in Cancer," FEBS Journal, 2012, vol. 279, pp. 2610-2623.

Wang, B., et al., "Detection of Lipid in Atherosclerotic Vessels Using Ultrasound-Guided Spectroscopic Intravascular Photoacoustic Imaging," Optics Express, Mar. 2010, vol. 18, No. 5, pp. 4889-4897.

Wang, L., et al., "Fast Voice-Coil Scanning Optical-Resolution Photoacoustic Microscopy," Optics Letters, Jan. 2011, vol. 36, No. 2, pp. 139-141.

Wang, L., et al., "Photoacoustic Tomography: In Vivo Imaging From Organelles to Organs," SCIENCE, Mar. 2012, vol. 335, pp. 1458-1462.

Wang, H., et al., "Reflection-Mode Optical-Resolution Photoacoustic Microscopy Based on a Reflective Objective," Optics Express, Oct. 2013, vol. 21, No. 20, 9 pages.

Wang, H-W, et al., "Label-Free Bond-Selective Imaging by Listening to Vibrationally Excited Molecules," Physical Review Letters, 2011, vol. 106, pp. 238106-1 through 238106-4.

Xu, Z., et al., "Photoacoustic Tomography of Water in Phantoms and Tissue," Journal of Biomedical Optics, May/Jun. 2010, vol. 15, No. 3, pp. 036019-1 through 036019-6.

Yao, D-K, et al., "In Vivo Label-Free Photoacoustic Microscopy of Cell Nuclei by Excitation of DNA and RNA," Optics Letters, Dec. 2010, vol. 35, No. 24, pp. 4139-4141.

(56) References Cited

OTHER PUBLICATIONS

Yao, D-K, et al., "Optimal Ultraviolet Wavelength for In Vivo Photoacoustic Imaging of Cell Nuclei," Journal of Biomedical Optics, May 2012, vol. 17, No. 5, pp. 056004-1 through 056004-7.

Zhang, H.F., et al., "Imaging of Hemoglobin Oxygen Saturation Variations in Single Vessels In Vivo Using Photoacoustic Microscopy," Applied Physics Letters, 2007, vol. 90, No. 5, pp. 053901-1 through 053901-3.

Zink, D., et al., "Nuclear Structure in Cancer Cells," Nature Reviews, Cancer, Sep. 2004, vol. 4, pp. 677-687.

* cited by examiner

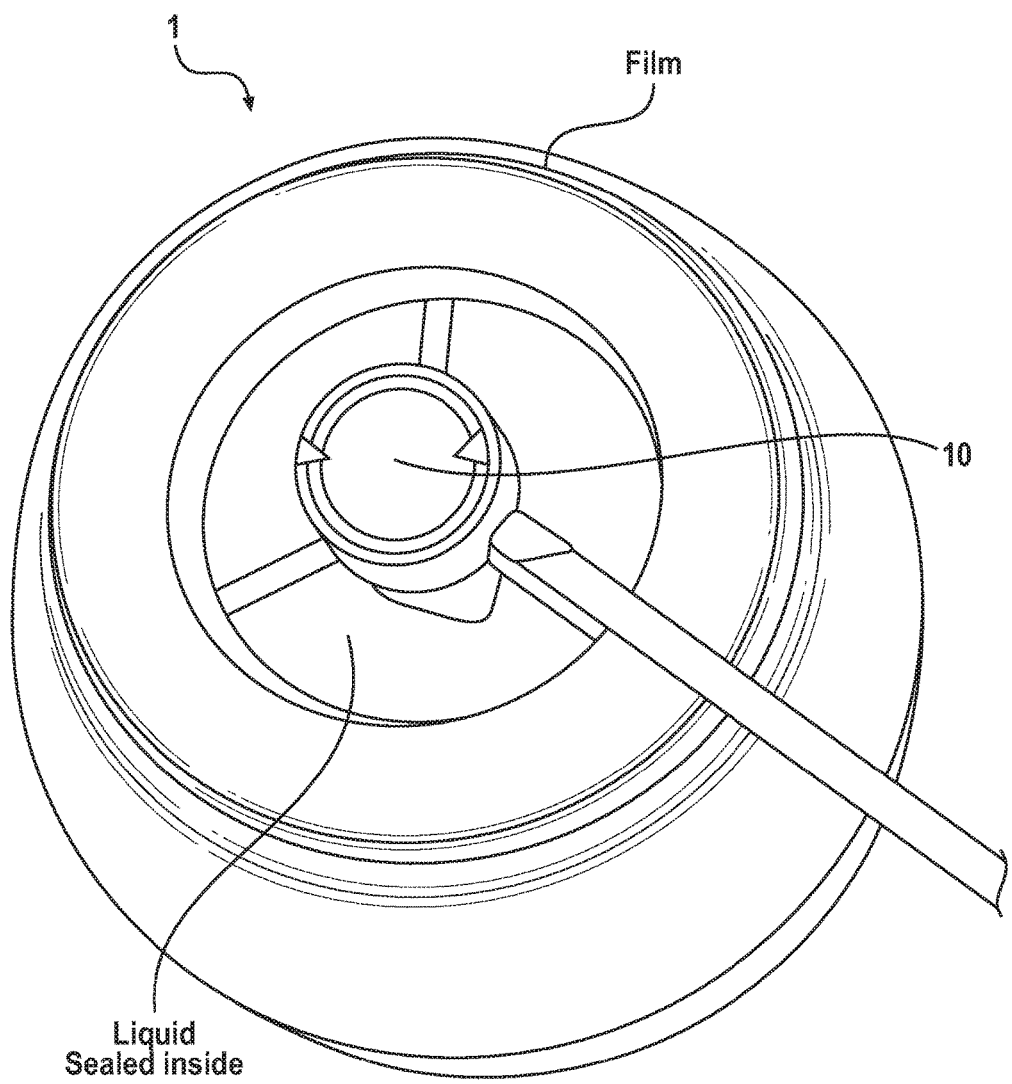

| Symbol | Feature |
|---|---|
| ▬ ▬ ▬ ▬ | Ultraviolet Path |
| ▪▪▪▪▪▪▪▪ | Visible Path |
| ············ | Near-Infrared Path |
| ─ ─ ─ ─ | Visible and Near-Infrared Combined Path |
| ══════ | Combined Path in All Three Spectral Range |
| OPO | Optical Parametric Oscillator |
| FM | Flip Mirror |
| DM | Dichroic Mirror |
| M1 | Mirror |
| M2 | Mirror |
| RP | Right-angle prism |
| OAO | Optical-acoustic objective 1 |

SYSTEMS AND METHODS FOR MULTISPECTRAL PHOTOACOUSTIC MICROSCOPY

CROSS-REFERENCE TO RELATED APPLICATIONS

This application is a U.S. National Stage Application of and claims the benefit of International Patent Application No. PCT/US2015/064543, filed Dec. 8, 2015, which claims priority to and benefit of U.S. Provisional Patent Application Ser. No. 62/088,722, filed Dec. 8, 2014, the entire contents and substance of which are incorporated by reference in their entirety as if fully set forth below.

FIELD

The disclosed technology generally relates to photoacoustic microscopy (PAM).

BACKGROUND

Photoacoustic microscopy (PAM) has been used in recent years to satisfy a need in high-resolution imaging of endogenous optical absorption contrasts in vivo, among which DNA/RNA, hemoglobin, and lipid may be of particular interest. Specifically, a cell nucleus may be a critical organelle containing DNA genome, which strongly absorbs ultraviolet light. Additionally, morphological changes in cell nuclei, including enlargement and envelope folding, are considered hallmarks of cancer cells.

Hemoglobin, a dominant absorber in the visible spectral range, is the primary oxygen carrier in the blood circulation. Angiogenesis and hypoxia, which can be respectively revealed by the distribution and oxygen saturation of hemoglobin, are also core indicators of cancer. Further, lipid forms a diverse group of infrared-absorbing molecules that play important roles at cellular and organismal levels. Aberrant lipid metabolism therefore can establish hallmarks of cancer cells.

Concurrent imaging of the multiple endogenous optical absorbers at the same spatial scale may be promising for both basic and translational cancer research. However, multispectral PAM modalities with ultraviolet to near-infrared spectral ranges have been difficult to implement in practice due to complications caused by the chromatic aberration of the optics. It is with respect to these and other considerations that the various embodiments described below are presented.

SUMMARY

In some aspects, the disclosed technology relates to multispectral PAM systems and methods. In one aspect, the disclosed technology relates to a multispectral PAM system which, in one embodiment, comprises a reflective microscope objective with approximately zero chromatic aberration. The objective may be employed to achieve consistent optical focusing over a broad spectral range (e.g., from ultraviolet to near-infrared spectrums). The system may comprise an ultrasonic transducer attached to a dark zone of the reflective microscope objective for easy, convenient confocal alignment of the optical excitation and acoustic detection in reflection mode. The transducer may be customizable. Attaching and aligning the transducer and objective as described can avoid the optical aberration and acoustic loss induced by otherwise needed optical-acoustic beam combiners in conventional PAM systems.

With a high-repetition-rate wavelength-tunable optical parametric oscillator (OPO) laser, systems and methods according to some embodiments of the disclosed technology may cover a spectral range of 270-1300 nm. A lateral resolution of approximately 2.8 μm may be nearly constant and has been achieved experimentally. Capitalizing on the ultrabroad spectral range and corresponding consistent spatial resolution, concurrent PAM using the herein disclosed system and methodologies is capable with cell nuclei (DNA/RNA contrast at 270 nm), blood vessel (hemoglobin contrast at 532 nm), and sebaceous gland (lipid contrast at 1260 nm) at the same spatial scale in vivo (e.g., in an ear of a mammal such as a mouse).

When used with a wavelength-tunable optical-parametric-oscillator laser, multispectral PAM over an ultrabroad spectral range as well as a near-constant lateral resolution of approximately 2.8 μm is feasible. In some embodiments, multispectral PAM is capable of being used in the ultraviolet, visible, and near-infrared range to allow label-free concurrent imaging of cell nucleus (DNA/RNA contrast at 270 nm), blood vessel (hemoglobin contrast at 532 nm), and sebaceous gland (lipid contrast at 1260 nm) at the same spatial scale in vivo.

In some embodiments, a reflection-mode multispectral photoacoustic microscopy (PAM) system is disclosed having a reflective microscope objective. An ultrasonic transducer may be attached to a primary reflective surface of the reflective microscope objective so that a plurality of optical paths may be formed between the primary reflective surface and a plurality of internally positioned reflective surfaces. An optical and acoustic foci may be positioned opposite the internally positioned reflective surfaces so that an acoustic path is formed between the ultrasonic transducer and the optical and acoustic foci.

The ultrasonic transducer and the reflective microscope objective may be formed together in a single housing at a predetermined confocal alignment. The ultrasonic transducer may also be positioned in communication with, or within, an optically dark zone of the reflective microscope objective opposite the primary and internally positioned reflective surfaces.

The primary reflective surface of the reflective microscope objective may be a hemispherical mirror coated with ultraviolet enhanced material configured to cause an obscuration of one of the optical paths as well as a center of an incoming optical path of an optical system. The associated optical system in this embodiment may include a laser beam.

In other embodiments, the PAM system may include approximately zero chromatic aberration over a broad spectral range. The broad spectral range may be in a range between 200 nm-20 μm or the range may be 270-1300 nm. However, any number of ranges are contemplated as needed or required.

The reflective microscope objective may also include a nearly constant lateral resolution (e.g., approximately 2.8 μm). A focal length of the ultrasonic transducer and/or confocal alignment between the objective and the ultrasonic transducer may also be used to determine an optimized location where the ultrasonic transducer is permanently attached to the primary reflective surface. Confocal alignment and coupling of acoustic energy may also define a predetermined optimized fixed location of the ultrasonic transducer.

In some embodiments, the reflective microscope objective may be immersed in a tank comprising transparent liquid for acoustic coupling. The tank may be filled with the transparent liquid and sealed with a film. The transparent liquid may be non-absorbing silicone oil. The film may be optically transparent over 270-2000 nm (e.g., a polyethylene membrane). An ultrasound gel may also be disposed between the film and the reflective microscope objective. In some embodiments, filling a cavity of the reflective microscope objective and the tank may serve to minimize, if not eliminate, any optical aberration induced by a refractive-index mismatch caused by an interface of the liquid of the tank and the cavity of the reflective microscope objective.

In some embodiments, an entrance pupil of the reflective microscope objective may be sealed with a fused-silica broadband optical window. The ultrasonic transducer may be a piezoelectric ceramic piston ultrasonic transducer with a two-layer quarter-wavelength matching. Additionally, the ultrasonic transducer may be spherically focused and/or may be customizable. In this respect, the ultrasonic transducer may be adjustable from a first frequency and a first acoustic focus to a second frequency and second acoustic focus, the second frequency being greater than the first frequency, and the second acoustic focus being tighter than the first acoustic focus.

The disclosed technology according to some embodiments is particularly advantageous as it is capable of imaging cell nuclei, blood vessel, and sebaceous gland at an equivalent spatial scale in vivo.

In another aspect, the disclosed technology relates to a reflection-mode multispectral photoacoustic microscopy (PAM) system which, in one embodiment, has an optical system with a predetermined wavelength range and an output. A reflective microscope objective is provided to receive and focus the output and an ultrasonic transducer may be attached to a primary reflective surface of the reflective microscope objective. A plurality of optical paths may be formed between the primary reflective surface and a plurality of internally positioned reflective surfaces. An optical and acoustic foci may be positioned opposite the internally positioned reflective surfaces so that an acoustic path can be formed between the ultrasonic transducer and the optical and acoustic foci.

In some embodiments, the optical system may include a first pair of flip mirrors, wherein prior to being received by the reflective microscope objective, the output of the optical system can be split into multiple paths by respective flip mirrors. A second pair of flip mirrors may also be provided in the optical system, wherein the multiple paths are combined via the second pair of flip mirrors to form a combined path. An iris may be provided to receive and spatially filter the combined path into a filtered combined path. One or more prisms may be provided to receive the filtered combined path and deliver the output of the optical system to the reflective microscope objective.

In this respect, the optical system may include a high-repetition-rate wavelength-tunable optical parametric oscillator (OPO) laser and/or include a wavelength coverage ranging between 210-2600 nm.

In some embodiments, the reflection-mode multispectral PAM system may also include a computing system configured to control output of the optical system and imaging of the reflection-mode multispectral PAM system. The computing system can include a processor in communication across a bus with a central processing unit, a graphics processing unit, a main memory, and a static memory. The computing system may also include a display unit and a user interface.

In another aspect, the disclosed technology relates to a method of reflective mode multispectral photoacoustic microscopy (PAM) imaging which, in one embodiment, includes aligning a reflective microscope objective with an ultrasonic transducer; attaching the ultrasonic transducer to a primary reflective surface of the reflective microscope objective; forming a plurality of optical paths between the primary reflective surface and a plurality of reflective surfaces positioned internal to a housing enclosing the reflective microscope objective and the ultrasonic transducer; forming an acoustic path between an optical and acoustic foci and the ultrasonic transducer, the optical and acoustic foci being positioned opposite the reflective surfaces positioned internal to the housing.

The method may also include positioning the ultrasonic transducer in communication with or within an optically dark zone of the reflective microscope objective opposite the primary and internally positioned reflective surfaces; pulsating an excitation from an optical system; the reflective microscope objecting receiving the excitation; and/or utilizing the excitation with the reflective microscope objective and the ultrasonic transducer to image a predetermined area of a subject with approximately zero chromatic aberration over a broad spectral range.

The predetermined area may include at least one of cell nuclei, blood vessels, and/or a sebaceous gland at an equivalent spatial scale in vivo. In this embodiment, concurrent imaging of multiple endogenous optical absorbers may be possible in the predetermined area at the same spatial scale in vivo. Additionally, the excitation may include ultraviolet, visible, and near-infrared spectral excitations so that the multiple endogenous optical absorbers can be cell nucleus, blood hemoglobin, and lipids.

The method may also include minimizing or eliminating any optical aberration induced by a refractive-index mismatch caused by an interface of the liquid of the tank by filling a cavity of the reflective microscope objective and the tank; sealing an entrance pupil of the reflective microscope objective with a fused-silica broadband optical window; and/or adjusting the ultrasonic transducer from a first frequency and a first acoustic focus to a second frequency and second acoustic focus, the second frequency being greater than the first frequency, and the second acoustic focus being relatively tighter than the first acoustic focus.

Other aspects and features of the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 1C depicts a perspective view of optical-acoustic objective in accordance with one embodiment of the disclosed technology.

DETAILED DESCRIPTION

Figure 1A:
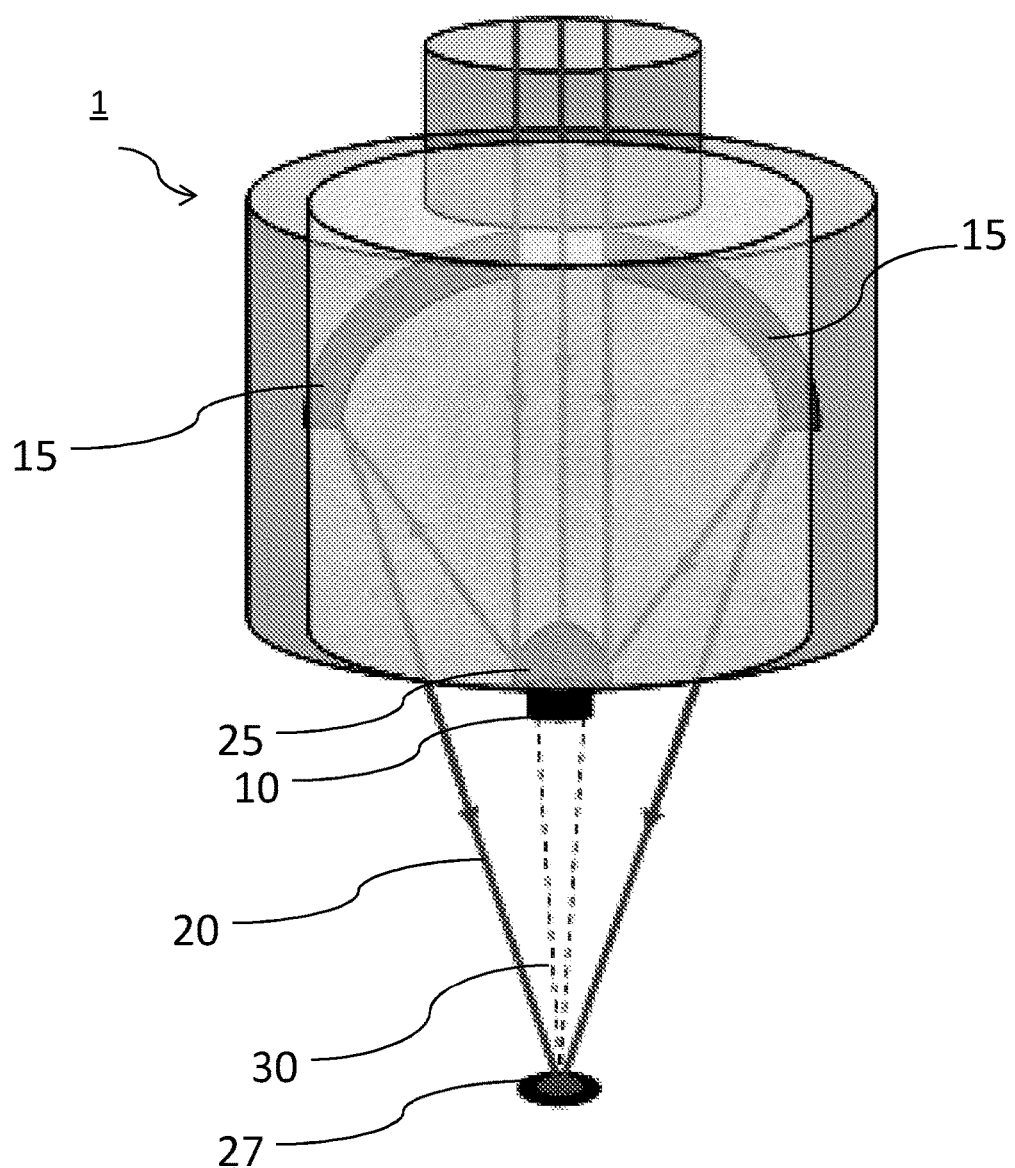
FIG. 1A depicts sectional view of an optical-acoustic objective in accordance with one embodiment of the disclosed technology.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other example embodiments include from the one particular value and/or to the other particular value.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

Figure 1B:
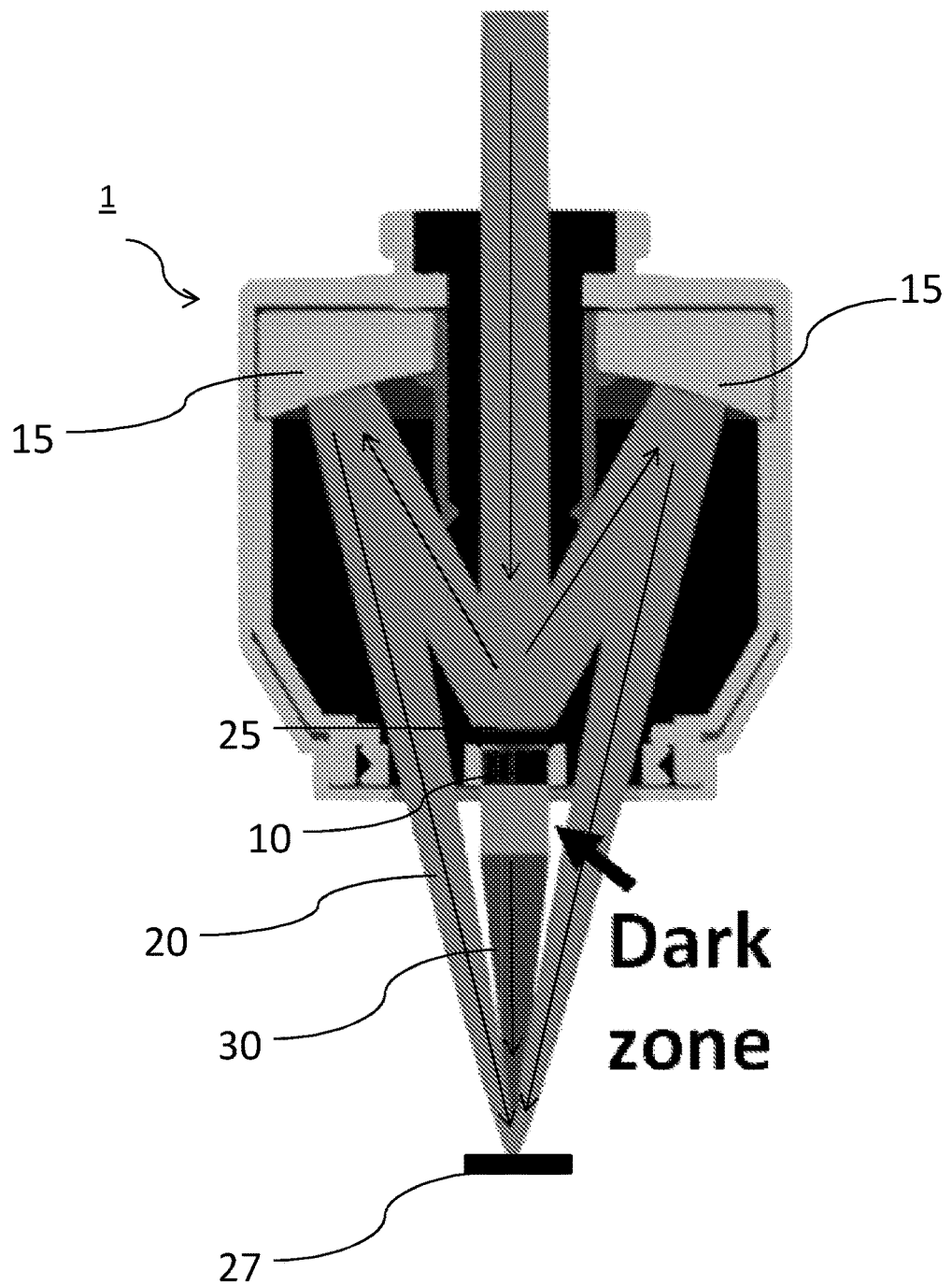
FIG. 1B depicts another sectional view an optical-acoustic objective in accordance with one embodiment of the disclosed technology.

In the following description, references are made to the accompanying drawings that form a part hereof and that show, by way of illustration, specific embodiments or examples. In referring to the drawings, like numerals represent like elements throughout the several figures. Turning to FIGS. 1A and 1B, a side plan sectional view of an optical-acoustic objective according to one embodiment of the present disclosure is shown. The objective 1 has a primary reflective surface 25. The objective 1 may be a reflective microscope objective (also known as Schwarzschild objective; e.g., LMM-15X-UVV, Thorlabs) in communication with an ultrasonic transducer 10. Transducer 10 may be customizable as needed or required. Internally positioned reflective surfaces 15 of the objective 1 may be provided in combination with transducer 10 and may be optically-reflective semi-circles for light focusing. Primary reflective surface 25 may be a hemispherical mirror(s) that is coated with ultraviolet-enhanced material such as aluminum. Coating surface 25 in this respect may ensure that objective 1 has approximately zero chromatic aberration over a broad spectral range such as 200 nm-20 μm. As can be seen in FIGS. 1A and 1B, ultrasonic transducer 10 may have optical 20 and acoustic 30 paths formed between transducer 10, surfaces 15 and 25 and optical and acoustic foci 27.

As can be seen, surface 25 may be a primary convex surface that causes an obscuration in the center of the imaging system 100. Thus, for example, a laser beam that enters through objective 1 may be solid only at the focus while being "donut-shaped" elsewhere after contacting surfaces 15 and/or 25. Transducer 10 may be attached to a rear surface of primary surface 25, which may be directly below the entrance pupil of the objective 1.

Positioning transducer 10 in the optically-dark zone, as shown in FIG. 1B, allows easy and convenient alignment of the optical and acoustic foci with little to no interference. To ensure optimal superposition of the optical and acoustic foci, the focal length of transducer 10 may be carefully designed and the transducer location optimized before permanent attachment to the objective 1. Confocal alignment and coupling of acoustic energy to transducer 10 make the objective 1 ideally suited for reflection-mode PAM.

For acoustic coupling, objective 1 may be immersed in a transparent liquid and/or other acoustic coupling liquid. In this respect, the mismatch of optical refractive index at the interface between the liquid and the air cavity of the objective 1 may induce significant optical aberration, particularly during mechanical scan when the liquid surface is unstable. To resolve this, objective 1 may be filled with the same liquid and sealed with a thin film (e.g., OCA8146-2, Thorlabs). This thin film as seen in FIG. 1C may be optically transparent over 270-2000 nm.

Exemplary liquids contemplated for use include silicone oil that is non-absorbing and commonly used in oil-immersion microscope objectives (e.g., UPLSAPO30XSIR, Olympus). To avoid acoustic reflection and the lensing effect induced by the surface tension at the objective-oil interface of silicone oil when used as the liquid with objective 1, the entrance pupil of objective 1 may also sealed with a fused-silica broadband optical window (e.g., WG41050, Thorlabs).

In some embodiments, the transducer 10 may be a piezoelectric ceramic piston ultrasound transducer with a two-layer quarter-wavelength matching. Transducer 10 may be spherically focused to maximize the photoacoustic detection sensitivity. The focal length of transducer 10 may be carefully and/or incrementally adjusted to ensure superposition of the optical and acoustic foci. Transducer 10 may also embody alternative ultrasound transducer designs using different materials including single crystal piezoceramics and piezoelectric polymers, transducer technologies (e.g. capacitive micromachined ultrasound transducer), lenses, matching, backing layers, and the like.

Aligning optical and acoustic foci and coupling of acoustic energy to transducer 10 can make the optical-acoustic objective according to some embodiments specially equipped for photoacoustic microscopy. Moreover, in some embodiments, the objective may have a standard microscope thread (RMS), and as such may be readily adopted into commercial optical microscopes for concurrent multi-modal microscopy such as optical, ultrasound, and photoacoustic.

Figure 2:
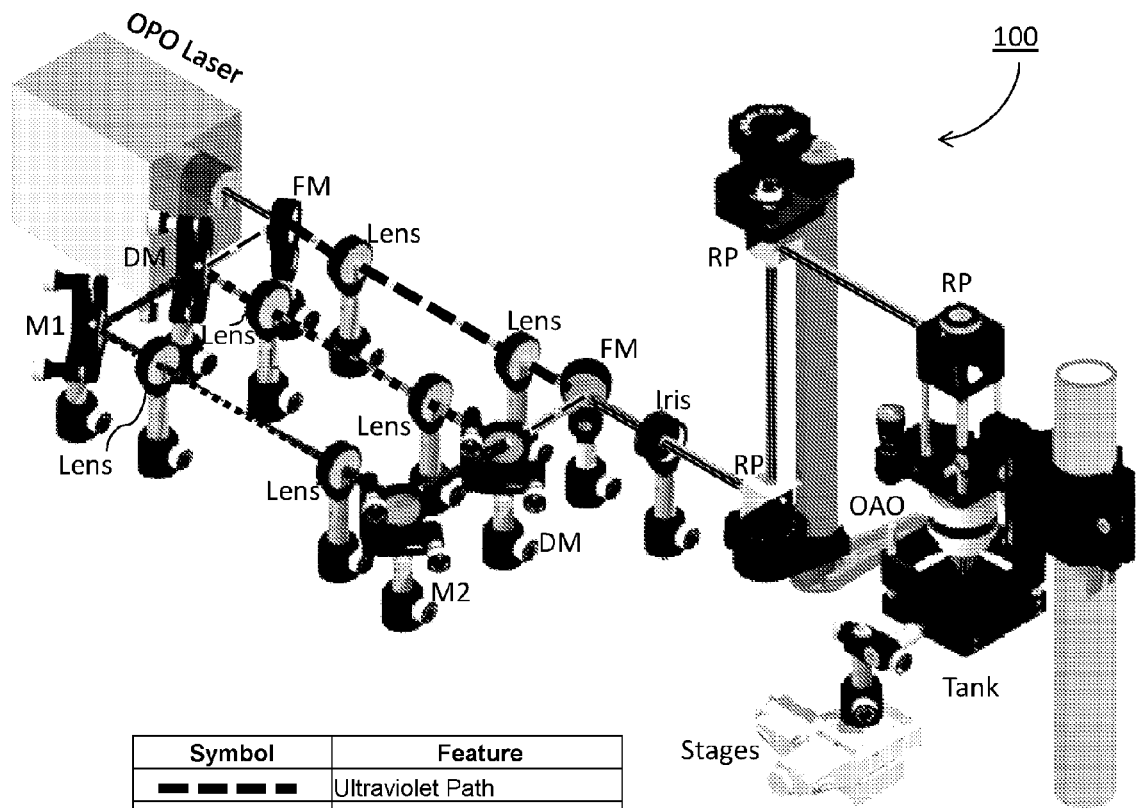
FIG. 2 depicts a schematic overview of a multispectral PAM system with an optical-acoustic objective, in accordance with one embodiment of the disclosed technology.

FIG. 2 depicts a schematic overview of a multispectral PAM system 100 with an optical-acoustic objective (OAO), in accordance with one embodiment of the disclosed technology. The OAO may be the same objective as the objective 1 described above according to embodiments shown with respect to FIGS. 1A-1C. The ultraviolet, visible, and near-infrared paths are labeled as indicated. The visible and near-infrared combined path and the combined path of all three spectral ranges are each likewise labeled in FIG. 2. Finally, optical parametric oscillator OPO, flip mirror FM, dichroic mirror DM, mirrors M1 and M2, and right-angle prism RP can be seen arranged with the OAO.

As can be seen, system 100 with OAO may employ a wavelength-tunable OPO laser (e.g., NT242, Ekspla), wherein the OPO laser may have wavelength coverage ranging between 210-2600 nm. Due to the non-uniform beam shape across the broad spectral range contemplated for use with system 100, the laser output may be split into multiple paths by flip mirror FM (e.g., TRF90, Thorlabs) and dichroic mirror FM (e.g., DMLP650, Thorlabs) as can be seen with respect to the depicted ultraviolet, visible, and near-infrared reshaped paths. The individually reshaped and expanded beams contemplated may be combined via another identical pair of FM and DM, spatially filtered by an iris (e.g., ID25, Thorlabs), reflected by three fused-silica broadband right-angle prisms (e.g., RP; PS611, Thorlabs), and focused by the optical-acoustic objective for multispectral photoacoustic excitation.

In some embodiments, the OAO may be immersed in a tank filled with a liquid (e.g., silicone oil) for acoustic coupling as shown in FIG. 2. In this respect, the bottom of the tank may be sealed with a thin transparent layer such as a polyethylene membrane to expose the object to be imaged. Positioning the objective as described and filling the cavity of the objective and corresponding tank with a transducer (e.g., transducer 10 of FIGS. 1A-1C) can minimize and/or eliminate optical aberration optical aberration induced by the refractive-index mismatch at the oil-cavity interface. An ultrasound gel (e.g., Aquasonic CLEAR®, Parker Laboratories) may also be used to be sandwiched or otherwise disposed between the membrane and object for acoustic coupling. The water tank and object holder may be mounted on stages such as one or more motorized linear stages for two-dimensional raster scanning (e.g., PLS-85, PI micos).

In some embodiments, by integrating an ultrasonic transducer as described above with respect to some embodiments with the reflective microscope objective, disclosed system is thereby capable of acoustic detection in the optically-dark zone with easy, convenient confocal alignment, and with little to no interference between the optical excitation and acoustic detection. Compared with existing optical-acoustic combining strategies, an optical-acoustic objective as described herein in accordance with some embodiments advantageously excels in low optical aberration and acoustic loss.

To that end, an optical-acoustic objective as described may result in approximately zero chromatic aberration for consistent optical resolution over a broad spectral range. This particularly renders the optical-acoustic objective in some embodiments ideal for multispectral measurements in a variety of applications including being used to image cell nuclei, blood vessel, and sebaceous gland at an equivalent spatial scale in vivo. In those embodiments where transducer 10 and optical objective 1 are fused into one solid piece, this also allows non-degradable PAM performance without routine confocal alignment of the optical and acoustic foci as required for traditional PAM. In addition, the objective can have has a standard microscope thread that can be easily adopted for convenient integration of PAM and other mainstream optical microscopy techniques, including but not limited to optical coherence tomography, confocal microscopy, and multiphoton microscopy.

In some embodiments, the axial resolution and sensitivity of multispectral PAM that results from an objective and corresponding transducer can be further improved by customizing the transducer with a higher-frequency with tighter acoustic focus. This can be particularly advantageous as it allows for the detection and differentiation of endogenous molecules with weak absorbance or overlapped absorption spectra, including but not limited to water, glucose, oxy- and deoxy-hemoglobin, and melanin. Combining the multiple endogenous absorption contrasts as described may provide additional insights into the pathogenic mechanisms of a broad spectrum of vascular and metabolic disorders at the cellular level.

An exemplary computing system may also be used with one or more embodiments of the objective, transducer, and other components as described herein as well as with other features for the multispectral PAM solution of system 100 and/or related methodologies that can be implemented therewith. Examples of this computing system can include logic, one or more components, circuits (e.g., modules), mechanisms, and the like. The computing system may include software residing (1) on a non-transitory computer readable storage medium or (2) in a transmission signal to execute certain actions of system 100, objective 1, and/or transducer 10, for example. The software, when executed, may cause computing system to actuate an optical system imaging by transmitting to and/or receiving information from an objective and/or transducer, as well as any corresponding predetermined test area of a subject.

In this respect, the computing system may include a general-purpose processor or other programmable processor) that can be temporarily configured (e.g., by software) to perform the certain operations of system 100, objective 1, and transducer 10. The various operations of the described computing system can be performed, at least partially, by one or more processors, wherein such processors can constitute processor-implemented circuits that operate to perform one or more operations or functions. In an example, the circuits referred to herein can comprise processor-implemented circuits.

Exemplary computing system components can include a processor (e.g., a central processing unit (CPU), a graphics processing unit (GPU) or both), memory, some or all of which can communicate with each other via a bus. A display unit and a user interface may also be provided to receive input from a user and/or our provide output to the user from the computing system as reflecting from PAM imaging when using corresponding system 100, objective 1, and/or transducer 10. Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary.

EXAMPLES

Various aspects of the disclosed technology may be still more fully understood from the following description of some example implementations and corresponding results. Some experimental data is presented herein for purposes of illustration and should not be construed as limiting the scope of the disclosed technology in any way or excluding any alternative or additional embodiments.

Figure 3:
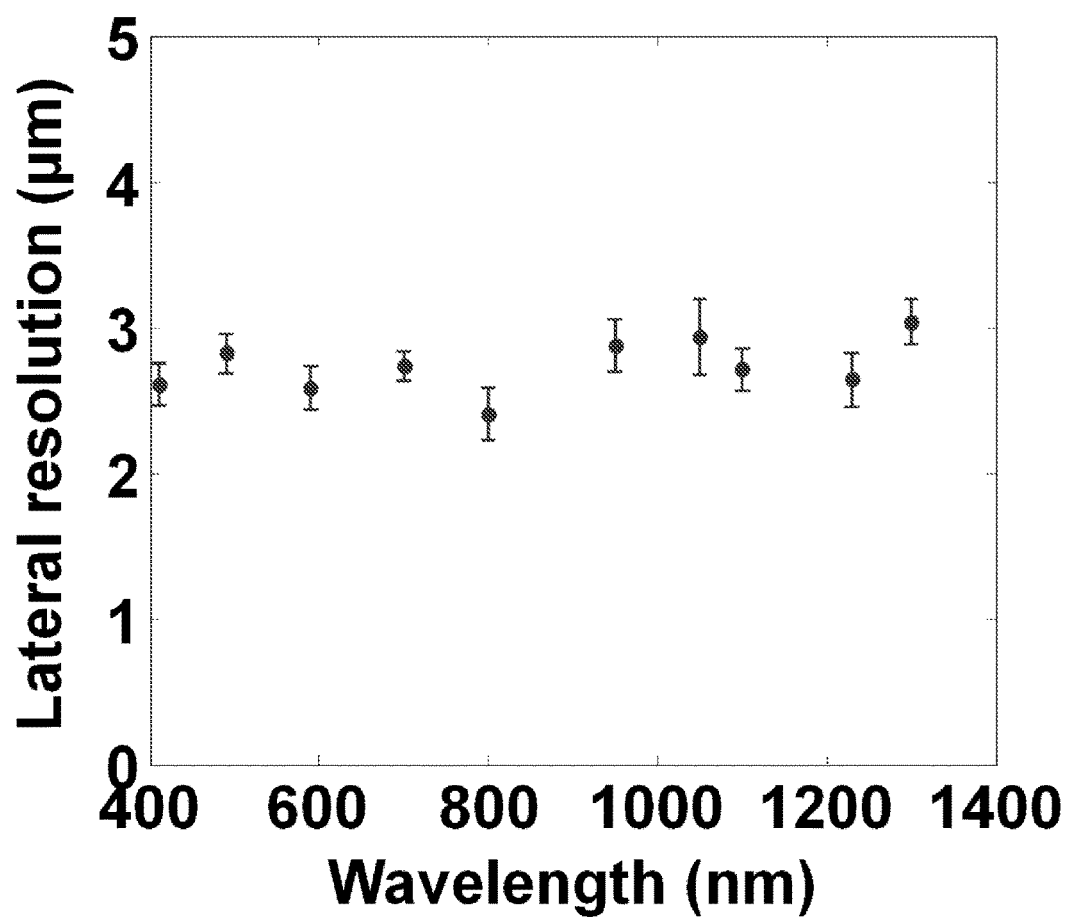
FIG. 3 is a graphical depiction of near-constant lateral resolution of multispectral PAM over a broad spectral range.

A first example of certain implementations of the disclosed technology and corresponding results will now be described with respect to FIG. 3, in which a graphical depiction is provided showing near-constant lateral resolution of multispectral PAM over a broad spectral range. It is understood that an objective in accordance with some embodiments described herein (e.g., objective 1 of FIGS. 1A-1C) may be ideal for spectroscopic fluorescence and/or photoacoustic microscopy as shown in FIG. 3. Specifically, FIG. 3 is a graphical depiction of experimentally determined optical lateral resolution of the optical-acoustic objective 1 of FIGS. 1A-1C, showing that the objective remains roughly constant over a wide spectral range. Optical focusing of the objective was evaluated by PAM of a 7 μm carbon fiber (S-CF706-T700, CST). To test its potential for multispectral imaging, the photoacoustic excitation wavelength was swept from 210 nm to 1400 nm with a spectral interval of approximately 100 nm. At each selected wavelength within the detectable range, a cross section of the fiber was repeatedly scanned 50 times. The mean values and standard errors of the measured diameter of the optical focus are shown in FIG. 3.

As can be seen, over the broad spectral range of 400-1300 nm, approximately zero chromatic aberration results in a near-constant optical focal diameter of approximately 2.8 μm, thereby rendering the objective in accordance with some embodiments ideal for concurrent PAM of multiple endogenous absorbers at the same spatial scale in vivo.

Figure 4:
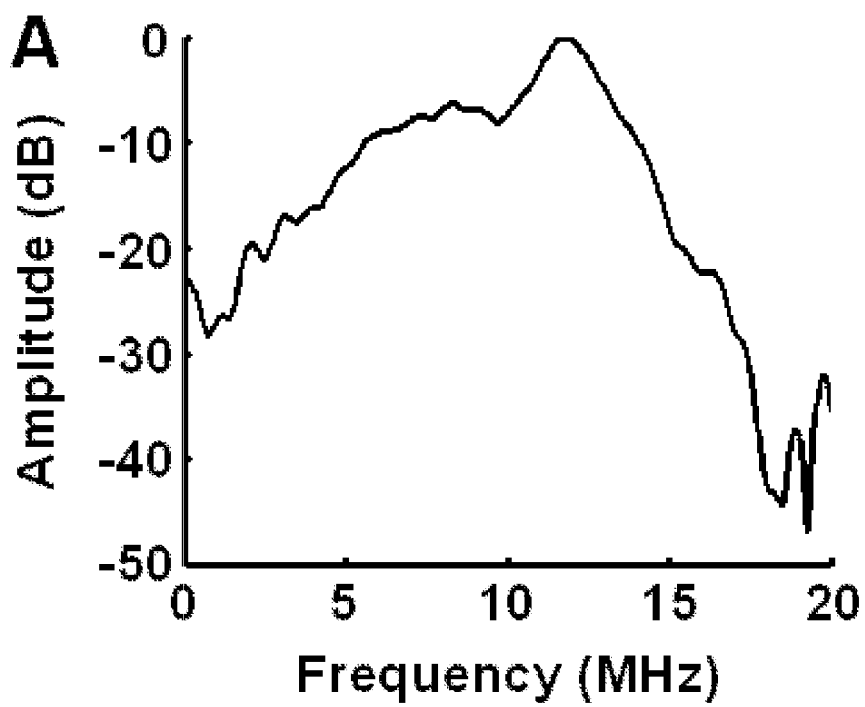
FIG. 4A depicts the frequency response of an ultrasonic transducer of an optical-acoustic objective in accordance with one embodiment of the disclosed technology.
FIG. 4B depicts a transverse acoustic-detection field of an ultrasonic transducer of an optical-acoustic objective in accordance with one embodiment of the disclosed technology.
Figure 4:
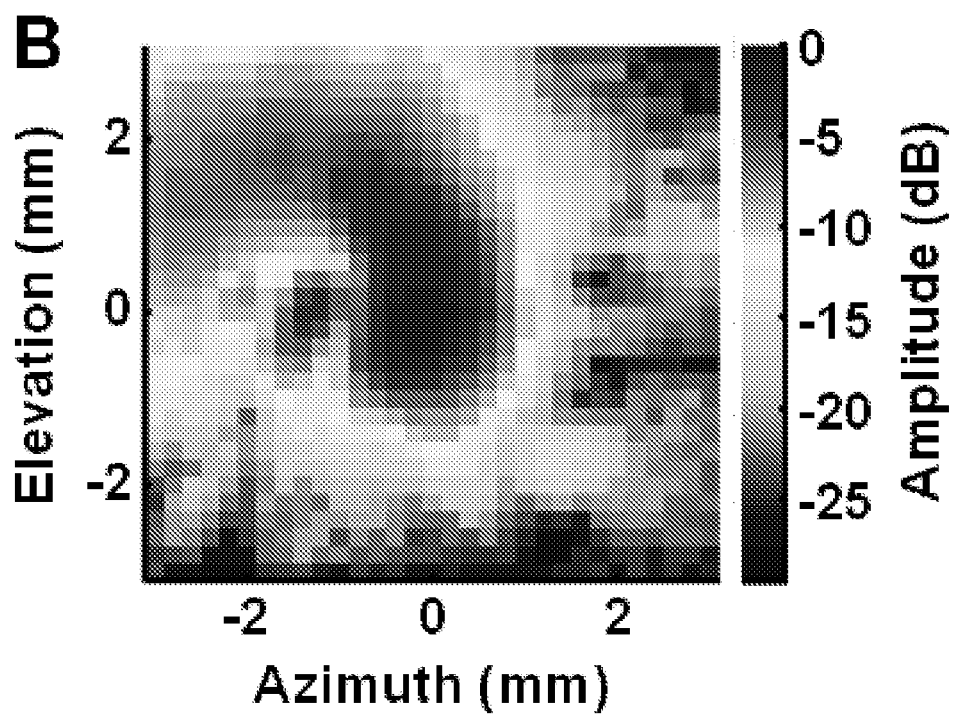

A second example of certain implementations of the disclosed technology will now be described with respect to FIGS. 4A and 4B, which included evaluations to characterize acoustic performance of an optical-acoustic objective according to an embodiment of the disclosed technology. More specifically, the frequency response of transducer 10 (FIGS. 1A-1C) that was customized is characterized using an ultrasonic pulser-receiver (5900PR, Panametrics). Measured data graphically depicted in FIG. 4A revealed a central frequency of approximately 11.8 MHz and a 6-dB bandwidth of 24%. The acoustic-detection field of the transducer was scanned using a commercial hydrophone transducer (HGL-0085, ONDA; bandwidth: 0.5 KHz-40 MHz) motorized by a three-dimensional linear stage. The 6-dB acoustic beam width along the azimuthal and elevational directions used were 1.5 mm and 2.5 mm, respectively, as shown in FIG. 4B. The distance measured between the acoustic focal plane and back surface of transducer was approximately 24 mm matching the working distance of reflective microscope objective 1 for the confocal alignment of the optical and acoustic foci.

Figure 7:
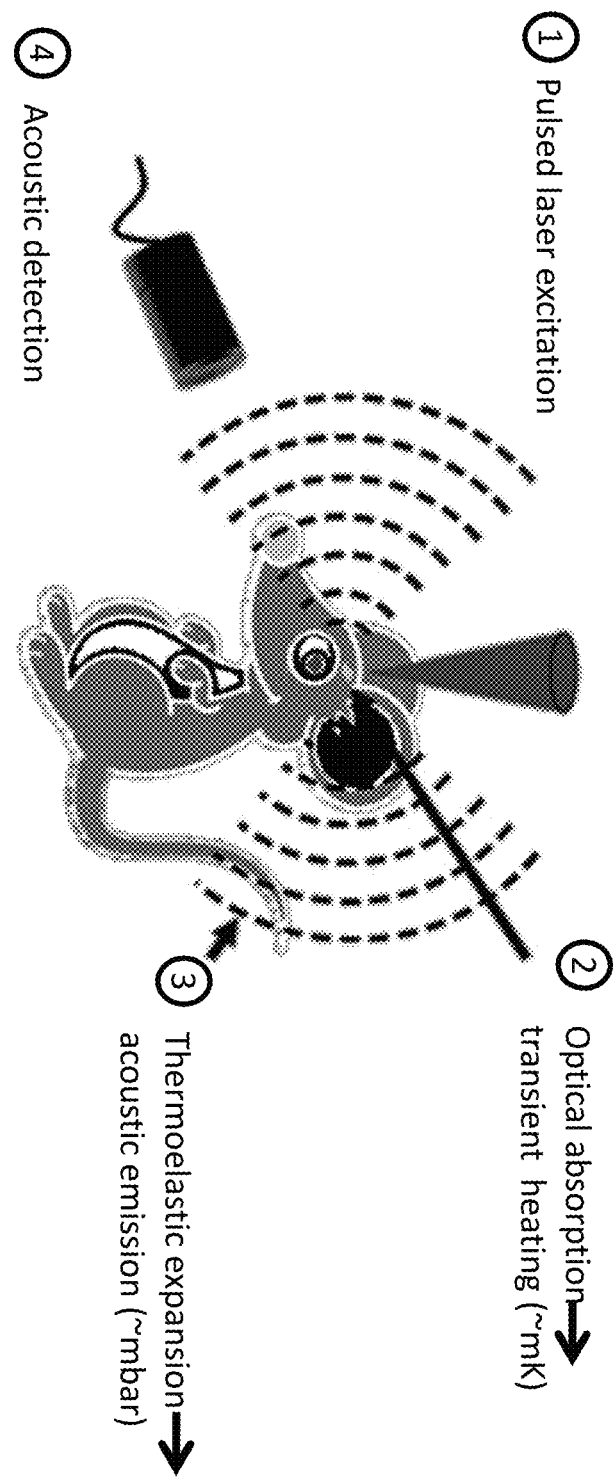
FIG. 7 depicts a schematic overview of photoacoustic imaging during testing.
Figure 8:
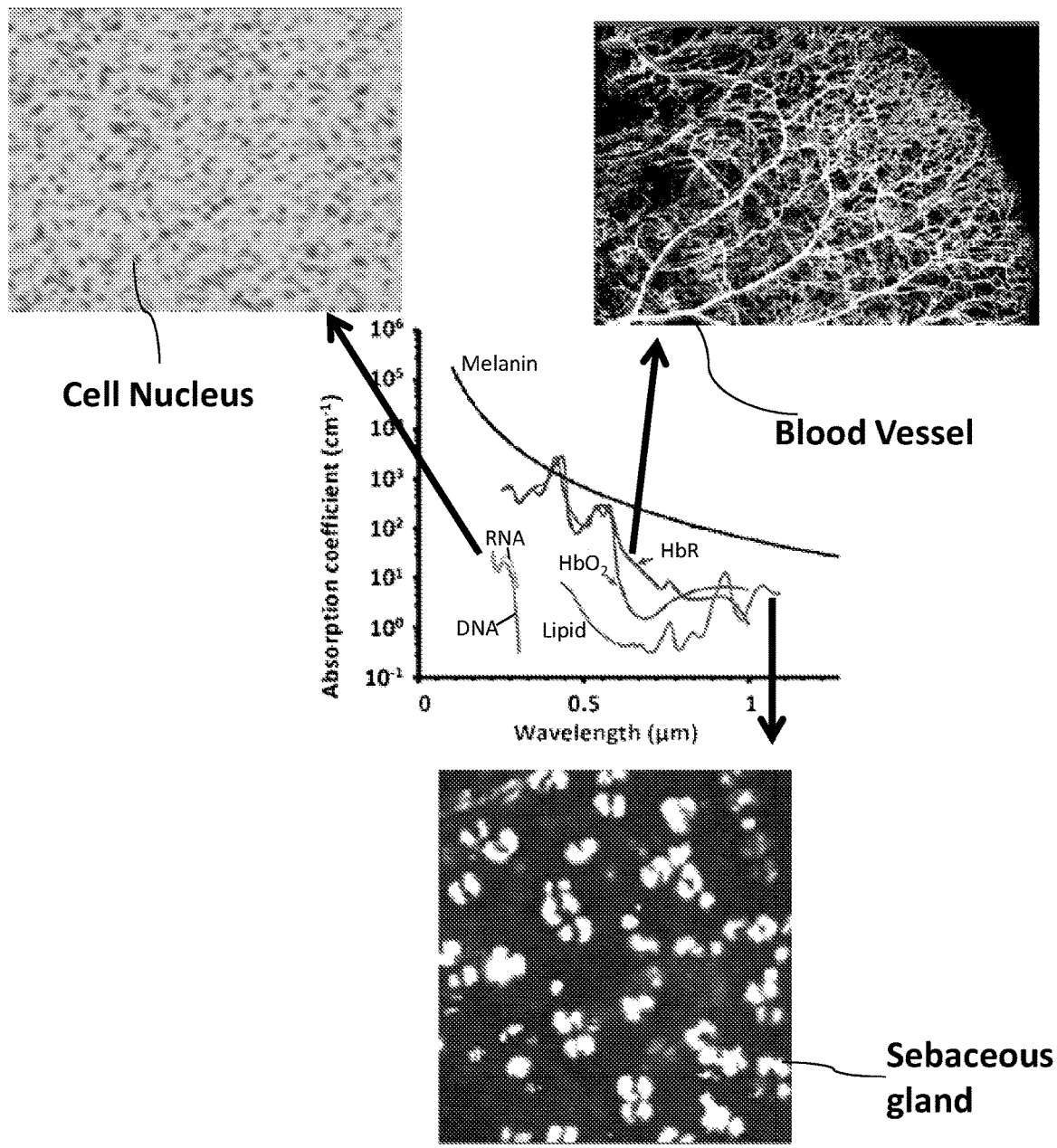
FIG. 8 depicts endogenous absorption contrasts including cell nuclei, blood vessels, and the sebaceous gland during testing as discussed with regards to FIGS. 5-7.
Figure 9:
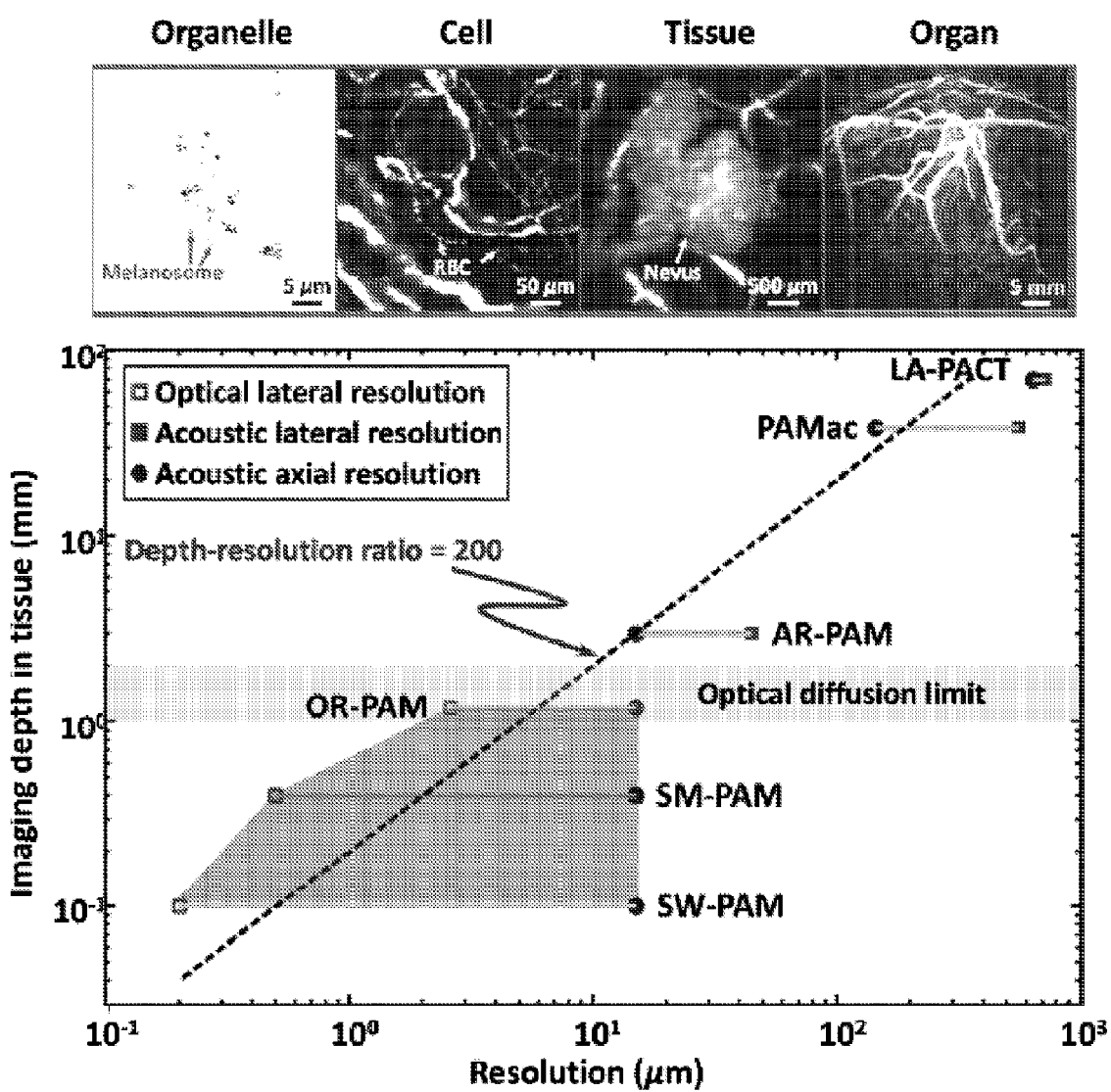
FIG. 9 graphically depicts spatial scalability of photoacoustic imaging with exemplary subjects such as organelles, cells, tissue, and organs during testing as discussed with regards to FIGS. 5-7.
Figure 10:
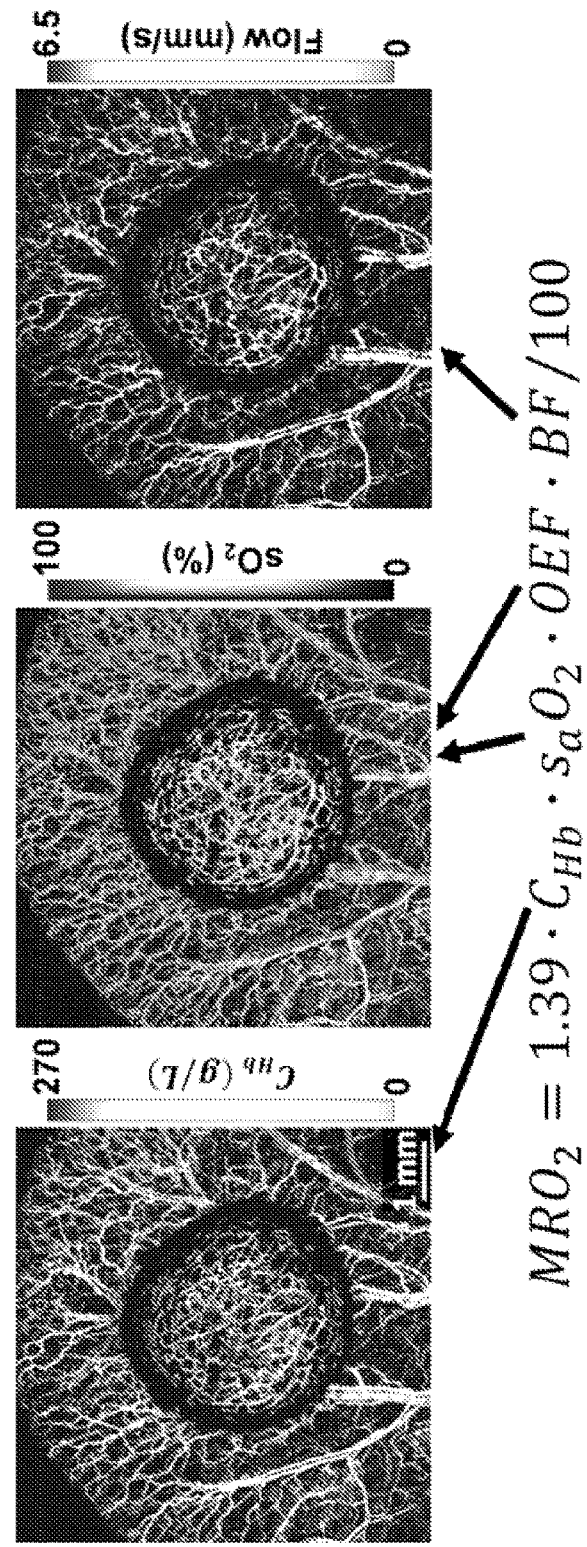
FIG. 10 depicts multi-parametric photoacoustic microscopy of cancer during testing as discussed with regards to FIGS. 5-7.

The in vivo performance of the multispectral PAM was also tested in the ear of a nude mouse (Crl:NU-Foxn1$^{nu}$, Charles River Laboratories; 6-month old), wherein a schematic overview of said testing is depicted in FIG. 7. Throughout the experiment, the mouse was maintained under anesthesia with 1.2% vaporized isoflurane and the body temperature was set at 37° C. using a heating pad. Three major endogenous optical absorbers—cell nucleus, blood hemoglobin, and lipid—were imaged using an optical system pulsed with laser excitations with the objective shown in FIGS. 1A-1C and corresponding modalities with ultraviolet, visible, and near-infrared excitations, wherein optical absorption and thermoelastic expansion was measured using the herein described acoustic detection. The results are depicted in FIGS. 5A though 5C as well as FIGS. 8-10.

Figure 5:
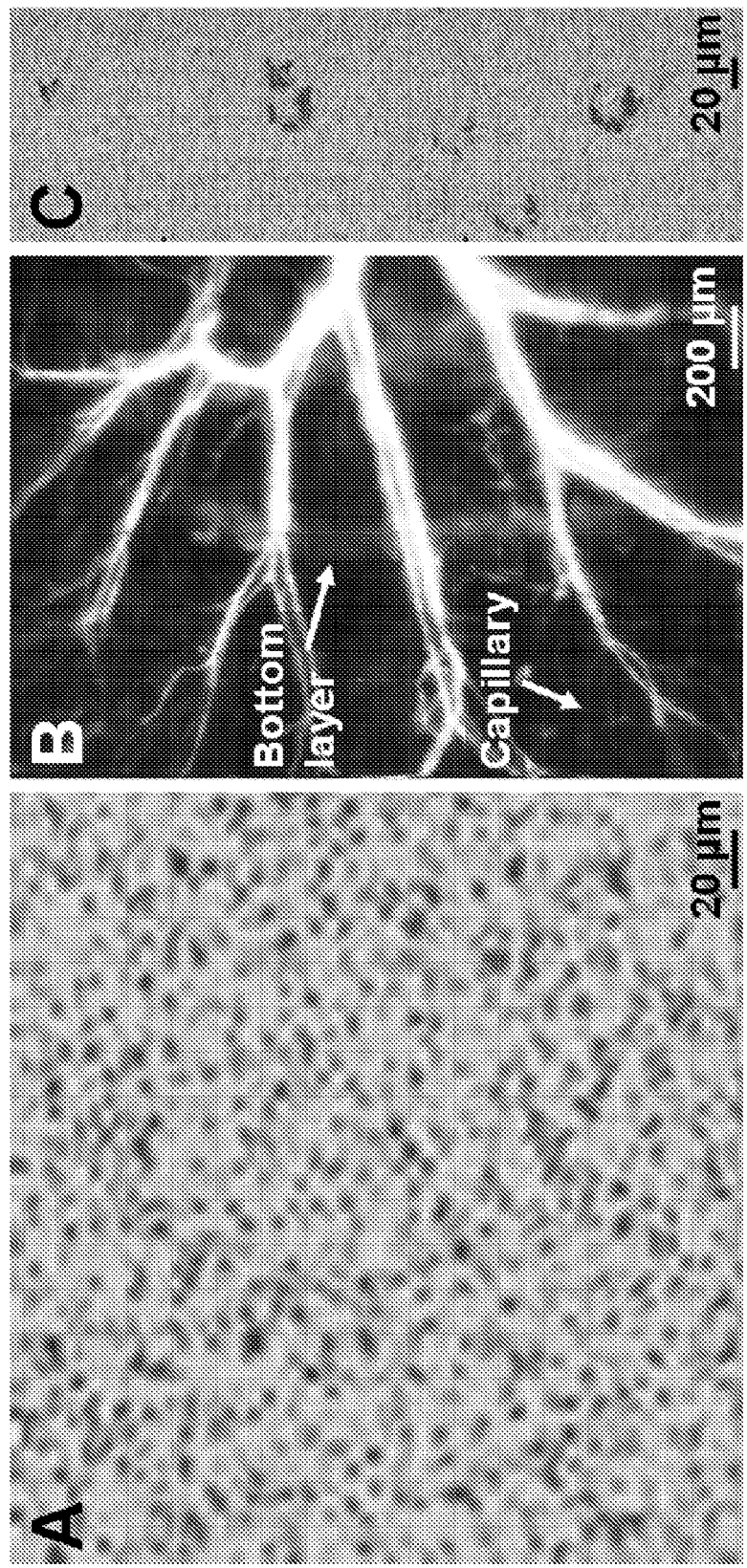
FIG. 5A depicts a multispectral PAM image of a cell nucleus of 270 nm.
FIG. 5B depicts a multispectral PAM image of a blood vessel of 532 nm.
FIG. 5C depicts a multispectral PAM image of a sebaceous gland of 1260 nm in a mouse ear in vivo.
Figure 6:
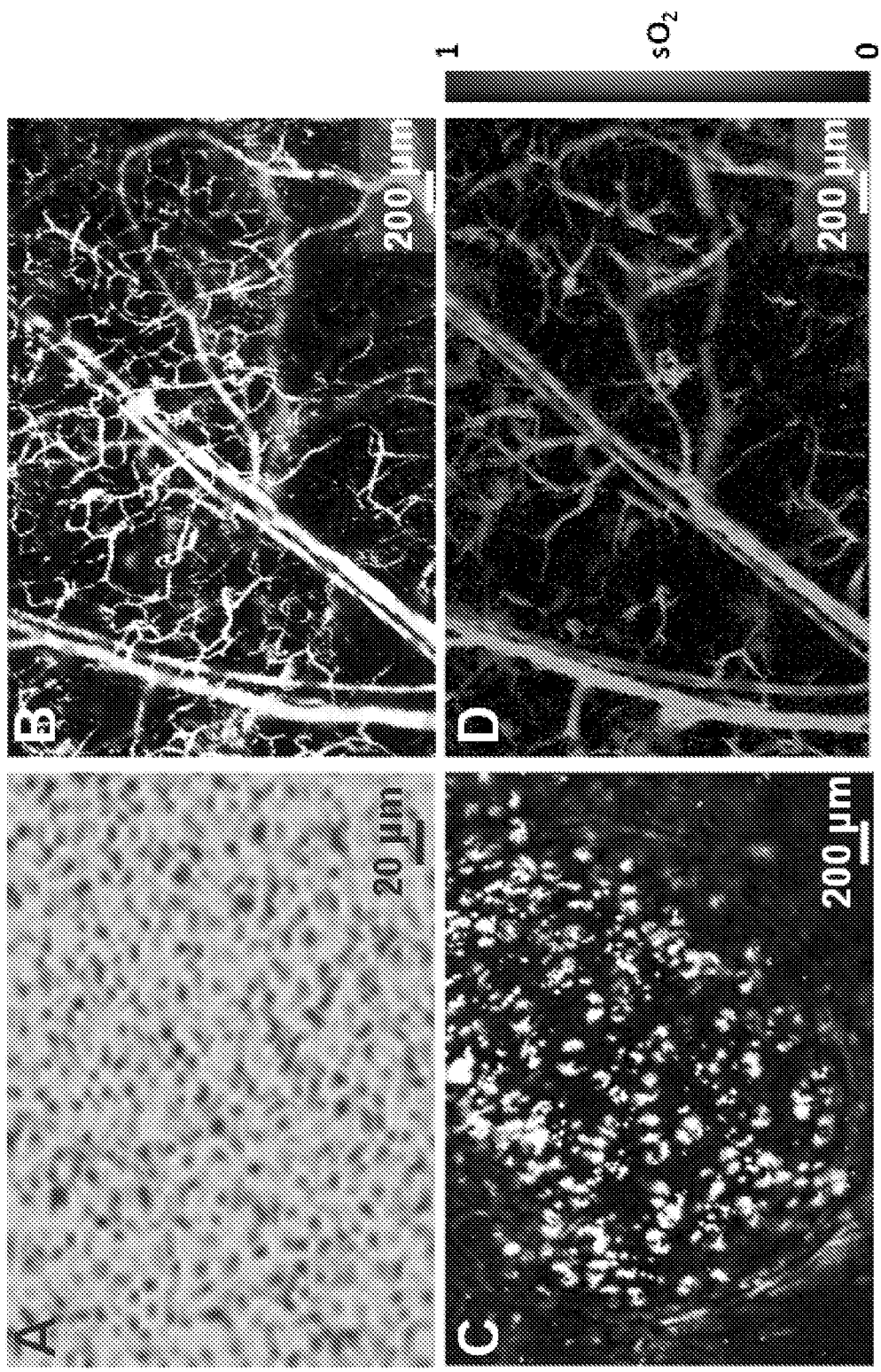
FIG. 6A depicts a multispectral PAM image of cell nucleus of 280 nm.
FIG. 6B depicts a multispectral PAM image of a blood vessel of 532 nm.
FIG. 6C depicts a multispectral PAM image of lipid of 1260 nm.
FIG. 6D depicts a multispectral PAM image of oxygen saturation of hemoglobin of 532 nm and 559 nm, respectively.

Specifically, the cell nucleus was imaged at 270 nm as seen in FIG. 5A where two major cellular components—DNA and RNA—have relatively high optical absorption. The imaged cell nuclei of FIG. 5A show a uniform distribution with an average diameter of approximately 6 μm. The vascular anatomy was also imaged at 532 nm as shown in FIG. 5B. The data of FIG. 5B revealed that an isosbestic wavelength of hemoglobin where oxy- and deoxy-hemoglobin absorb light equally. With 2.8 μm lateral resolution, the ear vasculature down to single capillaries was resolved using the objective 1 shown in FIGS. 1A-1C. Operating at a relatively low acoustic frequency, the herein disclosed multispectral PAM imaged both the top and bottom vascular layers of the subject's ear. The sebaceous gland was also imaged at 1260 nm as shown in FIG. 5C where the lipid absorption peaks. The unique U-shape of sebaceous glands was clearly observed and the relatively low optical absorption of silicone oil at the wavelength range 1200-1300 nm showed negligible attenuation to the laser excitation.

Similarly, FIGS. 6A through 6D depict the image quality with objective 1 (FIGS. 1A-1C) when used a wide spectral range. For example, FIGS. 6A-6D depict in vivo label-free images of a multispectral PAM of cellular nuclei of 280 nm, blood vessels of 532 nm, lipids 1260 nm, and oxygen saturation of hemoglobin (sO$_2$) of 532 nm and 559 nm, respectively. The graphical depictions of FIGS. 6A-6D were concurrently acquired in vivo at different wavelengths by a photoacoustic microscope similar to FIGS. 5A-5C.

REFERENCES

The disclosed technology in accordance with certain aspects and example embodiments may utilize one or more aspects disclosed in one or more of the following references, applications, publications and patents, which are hereby incorporated by reference herein in their entirety (and which are not admitted to be prior art with respect to the disclosed technology by their inclusion): Maslov K, Zhang HF, Hu S, Wang L V. Optical-resolution photoacoustic microscopy for in vivo imaging of single capillaries. Opt Lett 2008;33:929-31; Hu S, Maslov K, Wang L V. Second-generation optical-resolution photoacoustic microscopy with improved sensitivity and speed. Opt Lett 2011;36:1134-6; Wang L V., Hu S. Photoacoustic Tomography: In Vivo Imaging from Organelles to Organs. Science 2012;335:1458-62; Yao D-K, Maslov K, Shung KK, Zhou Q, Wang L V. In vivo label-free photoacoustic microscopy of cell nuclei by excitation of DNA and RNA. Opt Lett 2010;35:4139-41; Zhang HF, Maslov K, Sivaramakrishnan M, Stoica G, Wang L V. Imaging of hemoglobin oxygen saturation variations in single vessels in vivo using photoacoustic microscopy. Appl Phys Lett 2007;90:053901; Wang B, Su JL, Amirian J, Litovsky SH, Smalling R, Emelianov S. Detection of lipid in atherosclerotic vessels using ultrasound-guided spectroscopic intravascular photoacoustic imaging. Opt Express 2010;18:4889-97; Wang HW, Chai N, Wang P, Hu S, Dou W, Umulis D, et al. Label-free bond-selective imaging by listening to vibrationally excited molecules. Phys Rev Lett 2011;106; Zink D, Fischer AH, Nickerson J a. Nuclear structure in cancer cells. Nat Rev Cancer 2004;4:677-87; Oladipupo S, Hu S, Kovalski J, Yao J, Santeford A, Sohn RE, et al. VEGF is essential for hypoxia-inducible factor-mediated neovascularization but dispensable for endothelial sprouting. Proc Natl Acad Sci U S A 2011;108:13264-9; Oladipupo SS, Hu S, Santeford AC, Yao J, Kovalski JR, Shohet R V, et al. Conditional HIF-1 induction produces multistage neovascularization with stage-specific sensitivity to VEGFR inhibitors and myeloid cell independence. Blood 2011;117:4142-53; Li M-L, Oh J-T, Xie X, Ku G, Wang W, Li C, et al. Simultaneous Molecular and Hypoxia Imaging of Brain Tumors In Vivo Using Spectroscopic Photoacoustic Tomography. Proc IEEE 2008;96:481-9; Hanahan D, Weinberg RA. The Hallmarks of Cancer. Cell 2000;100:57-70; Santos CR, Schulze A. Lipid metabolism in cancer. FEBS J 2012;279:2610-23; Benjamin DI, Cozzo A, Ji X, Roberts LS, Louie SM, Mulvihill MM, et al. Ether lipid generating enzyme AGPS alters the balance of structural and signaling lipids to fuel cancer pathogenicity. Proc Natl Acad Sci 2013;110:14912-7; Wang L, Maslov K, Yao J, Rao B, Wang L V. Fast voice-coil scanning optical-resolution photoacoustic microscopy. Opt Lett 2011;36:139-41; Wang H, Yang X, Liu Y, Jiang B, Luo Q. Reflection-mode optical-resolution photoacoustic microscopy based on a reflective objective. Opt Express 2013;21:24210-8; Yao D-K, Chen R, Maslov K, Zhou Q, Wang L V. Optimal ultraviolet wavelength for in vivo photoacoustic imaging of cell nuclei. J Biomed Opt 2012;17:056004; Beard P. Biomedical photoacoustic imaging. Interface Focus 2011:rsfs20110028; Cai DK, Neyer a., Kuckuk R, Heise HM. Optical absorption in transparent PDMS materials applied for multimode waveguides fabrication. Opt Mater (Amst) 2008;30:1157-61; Li L, Yeh C, Hu S, Wang L, Soetikno BT, Chen R, et al. Fully motorized optical-resolution photoacoustic microscopy. Opt Lett 2014; 39:2117-20; Xu Z, Li C, Wang L V. Photoacoustic tomography of water in phantoms and tissue. J Biomed Opt n.d.;15:036019; Pleitez MA, Lieblein T, Bauer A, Hertzberg O, von Lilienfeld-Toal H, Mäntele W. In vivo noninvasive monitoring of glucose concentration in human epidermis by mid-infrared pulsed photoacoustic spectroscopy. Anal Chem 2013;85:1013-20; Oh J-T, Li M-L, Zhang HF, Maslov K, Stoica G, Wang L V. Three-dimensional dimensional imaging of skin melanoma in vivo by dual-wavelength photoacoustic microscopy. J Biomed Opt n.d.;11:34032; U.S. patent application Ser. No. 14/244,011 entitled "Intuitive Ultrasonic Imaging System and Related Method Thereof," filed Apr. 3, 2014; U.S. patent application Ser. No. 12/762, 135 entitled "Intuitive Ultrasonic Imaging System and Related Method Thereof," filed Apr. 16, 2010; U.S. Patent Application Publication No. 2010/0268086, Oct. 21, 2010; U.S. patent application Ser. No. 10/506,722 entitled "Intuitive Ultrasonic Imaging System and Related Method Thereof," filed Sep. 7, 2004; U.S. Pat. No. 7,699,776, issued Apr. 20, 2010; International Patent Application No. PCT/US2003/006607 entitled "An Intuitive Ultrasonic Imaging System and Related Method Thereof," filed Mar. 6, 2003; International Patent Application Publication No. WO 03/075769, Sep. 18, 2003; U.S. patent application Ser. No. 14/209,177 entitled "Efficient Architecture for 3D and Planar Ultrasonic Imaging—Synthetic Axial Acquisition and Method Thereof," filed Mar. 13, 2014; U.S. patent application Ser. No. 13/267,297 entitled "Efficient Architecture for 3D and Planar Ultrasonic Imaging—Synthetic Axial Acquisition and Method Thereof," filed Oct. 6, 2011; U.S. Patent Application Publication No. 2012/0029356, Feb. 2, 2012; U.S. patent application Ser. No. 11/245,266 entitled "Efficient Architecture for 3D and Planar Ultrasonic Imaging—Synthetic Axial Acquisition and Method Thereof," filed Oct. 5, 2005; U.S. Pat. No. 8,057,392, issued Nov. 15, 2011; International Patent Application No. PCT/US2005/036077 entitled "Efficient Architecture for 3D and Planar Ultrasonic Imaging—Synthetic Axial Acquisition and Method Thereof," filed Oct. 5, 2005; International Patent Application Publication No. WO 06/042067, Apr. 20, 2006; U.S. patent application Ser. No. 14/063,830 entitled "System for Treatment and Imaging Using Ultrasonic Energy and Microbubbles and Related Method Thereof," filed Oct. 25, 2013; U.S. Patent Application Publication No. 2014/0142468, May 22, 2014; U.S. patent application Ser. No. 13/386,391 entitled "Systems and Methods for Ultrasound Imaging and Insonation of Microbubbles," filed Jan. 20, 2012; U.S. Patent Application Publication No. 2012/0209116, Aug. 16, 2012; International Patent Application No. PCT/US2010/042783 entitled "Systems and Methods for Ultrasound Imaging and Insonation of Microbubbles," filed Jul. 21, 2010International Patent Application Publication No. WO 2011/011539, Jan. 27, 2011; U.S. patent application Ser. No. 12/739,128 entitled "System for Treatment and Imaging Using Ultrasonic Energy and Microbubbles and Related Method Thereof," filed Apr. 21, 2010; U.S. Pat. No. 8,622,911, issued Jan. 7, 2014; International Patent Application No. PCT/US2008/081189 entitled "System for Treatment and Imaging Using Ultrasonic Energy and Microbubbles and Related Method Thereof," filed Oct. 24, 2008; International Patent Application Publication No. WO 2009/055720, Apr. 30, 2009; U.S. patent application Ser. No. 14/113,672 entitled "Bone Surface Image Reconstruction Using Ultrasound," filed Oct. 24, 2013; U.S. Patent Application Publication No. 2014/0046186, Feb. 13, 2014; International Patent Application No. PCT/US2012/034945 entitled "Bone Surface Image Reconstruction Using Ultrasound," filed Apr. 25, 2012; International Patent Application Publication No. WO 2012/148985, Nov. 1, 2012; International Patent Application No. PCT/US2013/045576 entitled "Ultrasound Imaging of Specular-Reflecting Target," filed Jun. 13, 2013; International Patent Application Publication No. WO 2013/188625, Dec. 19, 2013; U.S. patent application Ser. No. entitled "Ultrasound Imaging of Specular-Reflecting Target," filed; U.S. patent application Ser. No. 13/329,965 entitled "Specialized, High Performance, Ultrasound Transducer Substrates and Related Method Thereof," filed Dec. 19, 2011; U.S. patent application Ser. No. 12/191,839 entitled "Specialized, High Performance, Ultrasound Transducer Substrates and Related Method Thereof," filed Aug. 14, 2008; U.S. Pat. No. 8,093,782, issued Jan. 10, 2012; U.S. patent application Ser. No. 13/210,890 entitled "Ultrasound Imaging Beam-Former Apparatus and Method," filed Aug. 16, 2011; U.S. Patent Application Publication No. 2012/0053460, Mar. 1, 2012; U.S. patent application Ser. No.

11/160,915 entitled "Ultrasound Imaging Beam-Former Apparatus and Method," filed Jul. 14, 2005; U.S. Patent Application Publication No. 2007/0016022, Jan. 18, 2007; International Patent Application No. PCT/US2004/000887 entitled "Ultrasound Imaging Beam-Former Apparatus and Method," filed Jan. 14, 2004; U.S. patent application Ser. No. 12/960,477 entitled "Tracked Ultrasound Vessel Imaging," filed Dec. 4, 2010; U.S. Patent Application Publication No. 2011/0137175, Jun. 9, 2011; U.S. patent application Ser. No. 12/664,146 entitled "System and Method for Combined ECG-Echo for Cardiac Diagnosis," filed Dec. 11, 2009; U.S. Patent Application Publication No. 2010/0168578, Jul. 1, 2010; International Patent Application No. PCT/US2008/066711 entitled "System and Method for Combined ECG-Echo for Cardiac Diagnosis," filed Jun. 12, 2008; International Patent Application Publication No. WO 2008/154632 Dec. 18, 2008; International Patent Application No. PCT/US2009/004731 entitled "Front End Circuitry for Imaging Systems and Methods of Use," filed Aug. 18, 2009; International Patent Application Publication No. WO 2010/021709, Feb. 25, 2010; U.S. patent application Ser. No. 12/543,452 entitled "Front End Circuitry for Imaging Systems and Methods of Use," filed Aug. 18, 2009; U.S. Patent Application Publication No. 2010/0063399, Mar. 11, 2010; U.S. patent application Ser. No. 11/840,079 entitled "Hybrid Dual Layer Diagnostic Ultrasound Transducer Array," filed Aug. 16, 2007; U.S. Pat. No. 7,750,537, issued Jul. 6, 2010; U.S. patent application Ser. No. 11/160,914 entitled "Ultrasonic Transducer Drive," filed Jul. 14, 2005; U.S. Patent Application Publication No. 2007/0016044, Jan. 18, 2007; International Patent Application No. PCT/US2004/000888 entitled "Ultrasonic Transducer Drive," filed Jan. 14, 2004; U.S. patent application Ser. No. 10/542,242 entitled "Efficient Ultrasound System for Two-Dimensional C-Scan Imaging and Related Method Thereof," filed Jul. 14, 2005; U.S. Pat. No. 7,402,136, issued Jul. 22, 2008; International Patent Application No. PCT/US2004/001002 entitled "Efficient Ultrasound System for Two-Dimensional C-Scan Imaging and Related Method Thereof," filed Jan. 15, 2004; and International Patent Application Publication No. WO 04/065978, Aug. 5, 2004.

It should be appreciated that any of the components or modules referred to with regards to the objective, transducer, tank, and/or reflective surfaces as discussed herein, may be integrally or separately formed with one another. Further, redundant functions or structures of the components or modules may be implemented. Any of the herein described features and their components discussed herein may take on all shapes to provide and meet the environmental, structural demands, and operational requirements. Moreover, locations and alignments of the various components may vary as desired or required.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. The scope of the present solution is indicated by the appended claims, rather than the foregoing description, and all changes that come within the meaning and range of equivalents thereof are intended to be embraced therein.

The definitions of the words or elements of the following claims are, therefore, defined in this specification to not only include the combination of elements which are literally set forth. It is also contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination(s).

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what incorporates the essential idea of the embodiments.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims.

What is claimed is:

1. A reflection-mode multispectral photoacoustic microscopy (PAM) system, comprising:
    a reflective microscope objective;
    an ultrasonic transducer attached to a primary reflective surface of the reflective microscope objective, wherein a plurality of optical paths are formed between the primary reflective surface and a plurality of internally positioned reflective surfaces, and wherein the primary reflective surface is a hemispherical mirror coated with ultraviolet enhanced material configured to cause an obscuration of one of the optical paths formed between the primary reflective surface and a center of an incoming optical path of an optical system; and
    an optical and acoustic foci positioned opposite the internally positioned reflective surfaces, wherein an acoustic path is formed between the ultrasonic transducer and the optical and acoustic foci.

2. The system of claim 1, wherein the ultrasonic transducer and the reflective microscope objective are formed together in a single housing at a predetermined confocal alignment.

3. The system of claim 1, wherein the ultrasonic transducer is positioned in communication with or within an optically dark zone of the reflective microscope objective opposite the primary and internally positioned reflective surfaces.

4. The system of claim 1, wherein the optical system comprises a laser beam.

5. The system of claim 1, wherein the PAM system comprises approximately zero chromatic aberration over a spectral range of 200 nm-20 µm.

6. The system of claim 5, wherein the spectral range is 270-1300 nm.

7. The system of claim 1, wherein the reflective microscope objective is configured with a nearly constant lateral resolution of approximately 2.8 μm.

8. The system of claim 1, wherein the reflective microscope objective is immersed in a tank comprising transparent liquid for acoustic coupling, wherein the tank is filled with the transparent liquid and sealed with a film.

9. The system of claim 8, wherein the transparent liquid is non-absorbing silicone oil.

10. The system of claim 8, wherein the film is optically transparent over 270-2000 nm.

11. The system of claim 10, wherein the film is a polyethylene membrane.

12. The system of claim 8, wherein an ultrasound gel is disposed between the film and the reflective microscope objective.

13. The system of claim 1, wherein an entrance pupil of the reflective microscope objective is sealed with a fused-silica broadband optical window.

14. The system of claim 1, wherein the ultrasonic transducer comprises a piezoelectric ceramic piston ultrasonic transducer with a two-layer quarter-wavelength matching.

15. The system of claim 1, wherein the ultrasonic transducer is spherically focused.

16. The system of claim 1, wherein the ultrasonic transducer is adjustable from a first frequency and a first acoustic focus to a second frequency and second acoustic focus, the second frequency being greater than the first frequency, and the second acoustic focus being tighter than the first acoustic focus.

17. A reflection-mode multispectral photoacoustic microscopy (PAM) system, comprising:

an optical system having a predetermined wavelength range and an output;

a reflective microscope objective configured to receive and focus the output from the optical system;

an ultrasonic transducer attached to a primary reflective surface of the reflective microscope objective, wherein a plurality of optical paths are formed between the primary reflective surface and a plurality of internally positioned reflective surfaces; and an optical and acoustic foci positioned opposite the internally positioned reflective surfaces, wherein an acoustic path is formed between the ultrasonic transducer and the optical and acoustic foci, wherein the optical system comprises:

a first pair of flip mirrors, wherein prior to being received by the reflective microscope objective, the output of the optical system is split into multiple paths by respective flip mirrors;

a second pair of flip mirrors, wherein the multiple paths are combined via the second pair of flip mirrors to form a combined path;

an iris configured to receive and spatially filter the combined path into a filtered combined path; and one or more prisms configured to receive the filtered combined path and deliver the output of the optical system to the reflective microscope objective.

18. The system of claim 17, wherein the optical system comprises a high-repetition-rate wavelength-tunable optical parametric oscillator (OPO) laser.

19. The system of claim 17, wherein the optical system has a wavelength coverage ranging between 210-2600 nm.

* * * * *